United States Patent
Shellenberger

(10) Patent No.: US 9,532,523 B2
(45) Date of Patent: Jan. 3, 2017

(54) EDIBLE BEAN LINE <11258> (VIBRANT)

(71) Applicant: AmeriSeed, LLC, Decatur, IL (US)

(72) Inventor: Ron Shellenberger, Kuna, ID (US)

(73) Assignee: ADM Edible Bean Specialties, Inc., Decatur, IL (US)

( * ) Notice: Subject to any disclaimer, the term of this patent is extended or adjusted under 35 U.S.C. 154(b) by 152 days.

(21) Appl. No.: 14/252,926

(22) Filed: Apr. 15, 2014

(65) Prior Publication Data

US 2015/0289467 A1    Oct. 15, 2015

(51) Int. Cl.
*A01H 5/10* (2006.01)
*C12N 5/04* (2006.01)
*A01H 1/02* (2006.01)

(52) U.S. Cl.
CPC *A01H 5/10* (2013.01); *A01H 1/02* (2013.01); *C12N 5/04* (2013.01)

(58) Field of Classification Search
None
See application file for complete search history.

(56) References Cited

U.S. PATENT DOCUMENTS 7,700,850 B2 *   4/2010   Webster ............... A01H 5/10
                                                           435/410
8,558,077 B2   10/2013   Shellenberger

OTHER PUBLICATIONS

Felicetti et al., Simple Sequence Repeats Linked with Slow Darkening Trait in Pinto Bean Discovered by Single Nucleotide Polymorphism Assay and Whole Genome Sequencing, Crpo Science, vol. 52, Jul.-Aug. 2012, pp. 1600-1608, USA.
Plant Variety Protection Office, PVP Certificate 201100007, Plant Variety Protection Office, pp. 1-23, Aug. 18, 2011, USA.

* cited by examiner

*Primary Examiner* — Stuart F Baum
(74) *Attorney, Agent, or Firm* — Andrew F. Niller

(57) ABSTRACT

An edible bean seed designated as <11258> or Vibrant, a sample of the edible bean deposited under accession no. PI 673082 is disclosed. Methods of using the edible bean seed designated as <11258> or Vibrant for breeding new varieties of bean seed are also disclosed, as well as seeds of the edible bean seed designated as <11258> or Vibrant.

15 Claims, 1 Drawing Sheet

```
                          SDP 1533
               ┌─────────────────────────────
 'Vibrant'     │
 <11258>───────┤
               │
               └─────────────────────────────
                          Sinaloa
```

EDIBLE BEAN LINE <11258> (VIBRANT)

TECHNICAL FIELD

The present invention relates generally to the field of plant breeding, and more specifically to edible bean line <11258> (Vibrant).

BACKGROUND OF THE INVENTION

In the United States, there is increasing concern over the consumption of high sugar and high fat foods by the population. An alarming increase in obesity among the citizens in the United States exists since many people in the United States are overweight due to a lack of exercise and poor eating habits.

Beans and peas are listed under both the Vegetables, and the Meats and Beans categories of the Dietary Guidelines Pyramid, thus, emphasizing the healthy nature of legumes in the diet. In addition to the emphasis on lower fat and lower sugar diets, beneficial effects of legumes are becoming apparent. Legumes are packed with fiber and protein, as well as being a good source of numerous vitamins and minerals. Legumes also have a low glycemic index and may help play a role in maintaining normal blood sugar levels; increasing digestive health; and even possibly improving heart health. Yet, legumes are an underutilized food in the United States diet.

One type of edible bean that is sold and consumed is the pinto bean. During storage, the seed coat of pinto beans may darken which may be viewed by consumers as a product flaw. Thus, needs exist for varieties of pinto beans that either do not darken or take longer to darken such that they are consumed before the seed coat darkens.

SUMMARY OF THE INVENTION

In each of its various embodiments, the present invention helps fulfill these needs and discloses a pinto bean variety for use in breeding new bean varieties, as well as a foodstuff.

In one embodiment, an edible bean seed designated as Vibrant, a sample of the edible bean seed deposited under accession no. PI 673082, is disclosed.

In another embodiment, methods of using the edible bean seed Vibrant for breeding new varieties of bean seed are disclosed. Seeds of the edible bean seed designated as Vibrant are also disclosed.

BRIEF DESCRIPTION OF THE DRAWINGS

FIG. 1 shows the breeding history of edible bean line <11258> (Vibrant) and its parents.

DETAILED DESCRIPTION OF THE INVENTION

In one embodiment, an edible bean line designated as <11258>, or (Vibrant), is disclosed. As used herein, the term Vibrant will be used to refer to edible bean variety <11258>. Also disclosed are bean plants having the physiological and morphological characteristics of the edible bean line designated as Vibrant. Parts of the bean plant including, without limitation, pollen, ovules, pods and cells, as well as uses of such parts in breeding are further disclosed.

In another embodiment, seed of the edible bean line designated as Vibrant is disclosed. Such seed may be an essentially homogenous population of the edible bean line designated as Vibrant, wherein such seed of the edible bean line designated as Vibrant is essentially free of other seed. Accordingly, the seed of the present invention comprises at least 95% or more of seed of the edible bean line designated as Vibrant.

In yet a further embodiment, tissue culture of regenerable cells of the edible bean line designated as Vibrant are disclosed. Such tissue culture may be capable of expressing all of the physiological and morphological characteristics of the edible bean line designated as Vibrant, and be capable of regenerating plants having the same genotype of plants of the edible bean line designated as Vibrant. The tissue culture may be obtained from embryos, meristems, cotyledons, pollen, leaves, anthers, roots, root tips, pistil, flower, seed and/or stalks.

In an additional embodiment, breeding methods for producing edible bean seeds, plants and/or pods using the edible bean line designated as Vibrant of the present invention as a parent are disclosed. Such breeding methods may be used to prepare hybrid edible bean seed or plants or inbred edible bean seed or plants, where seed ultimately produced using the edible bean line designated as Vibrant as at least one of the parents are included within the scope of this invention.

In one embodiment, methods of crossing the edible bean line designated as Vibrant with itself of a second plant and the seeds and plants produced by such methods are disclosed. Such methods may be used for propagating edible bean line designated as Vibrant, or can be used to produce hybrid dry bean seeds and the plants grown therefrom.

In a further embodiment, the present invention discloses a process for producing beans comprising obtaining a plant of the edible bean line designated as Vibrant, cultivating the plant to maturity, and collecting and/or harvesting beans from the mature plant. Such beans may be used ultimately as a foodstuff, as seed or as parent in a breeding program.

The present invention further discloses methods and compositions relating to plants, seeds and derivatives of edible bean line designated as Vibrant. This line has an erect growth habit, is indeterminate, has guides that are medium to long, and has no ability to climb. Vibrant is a pinto bean variety, exhibiting traits including, but not limited to, early season maturity and slow darkening. Observations and seed increase show that edible bean line designated as Vibrant shows uniformity and stability, without variants.

Origin and Breeding History.

The edible bean line designated as Vibrant exhibits improved traits including, without limitation, resistance to darkening of the seed coat conferred by presence of the recessive sd gene. The development of the edible bean line designated as Vibrant can be summarized as follows. A cross was made between ProVita's slow darkening pinto breeding line 'SDP 1533' as the female parent and the Ameriseed variety 'Sinaloa' as the male parent. The cross was made during the summer in Year 1 in the field. The edible bean line designated as Vibrant was derived from this cross.

The breeding history of edible bean line designated as Vibrant is shown in FIG. 1.

TABLE 1

The following Table indicates the selections used to produce the edible bean line designated as Vibrant.

| Year | Location | Generation | Bulk (lbs) | Single Plant Selections |
|---|---|---|---|---|
| Summer Year 1 | Twin Falls, ID-field | F1 | <2 lb | |
| Summer Year 2 | Twin Falls, ID-field | F2 | 3 lbs | |
| Summer Year 3 | Twin Falls, ID-field | F3 | | 5 single plant selections |
| Summer Year 4 | Twin Falls, ID-field | F4 | | 2 single plant selections |
| Summer Year 5 | Twin Falls, ID-field | F5 | 1.5 lbs | 2 single plant selections |
| Spring Year 6 | Kuna, ID-greenhouse | F6 | | |
| Summer Year 6 | Twin Falls, ID-field | F7 | 65.5 lbs | |
| Summer Year 7 | Twin Falls, ID-field | F8 | 1800 lbs | |
| Summer Year 8 | Twin Falls, ID-field | F9 | Commercial seed production | |

Selections were done in the F3, F4 and F5 generations as follows. In the F3 generation, there was segregation for architecture, maturity, seed size, and the slow darkening trait. Single plant selections were made for upright architecture, high pod set, yield, early maturity, and the slow darkening trait. In the F4 generation, single plant selections were made for upright architecture, high pod set, yield, early maturity, and the slow darkening trait. In the F5 generation, single plant selections were made for upright architecture, high pod set, yield, early maturity, and the slow darkening trait. Such selections resulted in the new edible bean line designated as Vibrant, which was observed to be uniform, stable and substantially free of any variants within commercially acceptable limits since the F9 generation. It is known that a small percentage of off-types may occur for a characteristic of edible bean line designated as Vibrant during multiplication.

Physiological and Morphological Characteristics of Edible Bean Line Designated as Vibrant.

Table 2 depicts the physiological and morphological characteristics of edible bean line designated as Vibrant.

TABLE 2

| Characteristic | Edible bean line designated as Vibrant |
|---|---|
| Market Class | Pinto |
| Maturity | Early (80-90 days) |
| Days from planting to harvest maturity | 90 |
| Plant Habit | |
| Type | Erect growth habit-indeterminate, guides medium to long with no ability to climb |
| Average height of mature plant | Not measured |
| Pod position | High (lower pods not touching soil surface) |
| Adaptability to machine harvest | Adapted |
| Lodging resistance | Good |
| Leaflet morphology | |
| Leaflet Shape | Smooth and semiglossy Ovate |
| Apex of leaflet | Acuminate |
| Base of leaflet | Obtuse |

TABLE 2-continued

| Characteristic | Edible bean line designated as Vibrant |
|---|---|
| Flower color and days to bloom | |
| Color of standard | White |
| Color of wings | White |
| Color of keel | White |
| Days to 50% bloom | 53 |
| Pod Morphology | |
| Green color pattern | Solid |
| Mature color pattern | Striped |
| Green primary color | Green |
| Mature primary color | Yellow |
| Green color modifier | Light medium |
| Mature color modifier | Light |
| Green secondary color | None |
| Mature secondary color | Red, faint red stripe when maturing |
| Green cross section shape | Pear |
| Mature cross section shape | Pear |
| Green pod curvature | Straight |
| Mature pod curvature | Straight |
| Green pod beak orientation | Curved downward |
| Mature pod beak orientation | Curved downward |
| Green constrictions | Slight |
| Mature constrictions | Slight |
| Average number of seeds/pod | 6.0 |
| Seed Color | Semishiny and polychrome |
| Primary color | White |
| Secondary color | Brown |
| Color pattern | Mottled |
| Hilar ring | Present |
| Hilar ring color | Yellow |
| Seed Shape and Weight | |
| Shape of seed taken from middle of pod | Cuboid |
| Dry seed weight in g/100 g Seeds (adjusted io 12% moisture) | 36 |
| Anthocyanin Pigmentation* | |
| Flowers | Absent |
| Leaves | Absent |
| Stems | Absent |
| Petioles | Absent |
| Pods | Present, faint red stripe when maturing |
| Peduncles | Absent |
| Seeds | Present |
| Nodes | Absent |
| Known Disease Reaction | None |

Vibrant possess a faint red stripe on a maturing pod, which may not be visible when the pod is dry.

Slow Darkening of Edible Bean Line Designated as Vibrant.

The edible bean line designated as Vibrant of the present invention carries a recessive sd gene that confers resistance to darkening due to age or environmental conditions. Such slow darkening is of particular benefit to pinto bean crops grown in environments that darken traditional pinto beans. Vibrant will retain improved bright white color through adverse weather conditions or upon storage, whereas the parent of Vibrant, Sinaloa, will darken significantly under such conditions.

Vibrant has faint red striping on the mature pods, whereas Sinaloa expresses more prominent red striping on the mature pods. Sinaloa also has expressed pigment in the stems, petioles, and peduncles, while Vibrant does not have pigment in the stems, petioles, or peduncles.

Deposit Information.

A deposit of the edible bean line designated as Vibrant of the present invention will be made with the National Center for Genetic Resources Preservation, Fort Collins, Colo. The date of deposit was Oct. 3, 2014. Upon issuance of a patent, all restrictions upon the deposit will be removed, and the deposit is intended to meet all of the requirements of 37 C.F.R. §1.801-1.809. The accession number for the deposited seeds of edible bean line designated as Vibrant is PI 673082. The deposit will be maintained in the depository for a period of 30 years, or 5 years after the last request, or for the enforceable life of the patent, whichever is longer, and will be replaced if necessary during such period.

The present invention has been described with reference to certain exemplary embodiments, legume products, compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiment, but rather by the appended claims as originally filed.

What is claimed is:

1. An edible bean seed designated as Vibrant, wherein a representative sample of the edible bean seed was deposited under the National Center for Genetic Resources Preservation accession no PI 673082.

2. A plant, or plant parts thereof, produced by growing the edible bean seed of claim 1.

3. Pollen of the plant of claim 2.

4. An edible bean plant, or plant parts thereof, having all of the physiological and morphological characteristics of the edible bean plant of claim 2.

5. A tissue culture of regenerable cells of the edible bean plant of claim 2.

6. The tissue culture of claim 5, wherein the cells are obtained from a plant part selected from the group consisting of leaf, pollen, embryo, meristematic cell, root, root tip, anther, stomatal cell, flower, seed, stem, pod and combinations of any thereof.

7. An edible bean plant regenerated from the tissue culture of claim 6, having all of the morphological and physiological characteristics of an edible bean plant grown from an edible bean seed designated as Vibrant, wherein a representative sample of the edible bean seed was deposited under the National Center for Genetic Resources Preservation accession no PI 673082.

8. A method for producing an edible bean seed comprising crossing two edible bean plants and harvesting the resulting edible bean seed, wherein at least one of the two edible bean plants is the edible bean plant of claim 2.

9. A method for producing a hybrid edible bean seed comprising crossing the edible bean plant of claim 2 with a second edible bean plant and harvesting the resulting hybrid edible bean seed.

10. A plurality of the edible bean seeds of claim 1.

11. A method of planting a field, comprising planting the plurality of the edible bean seeds of claim 10 in the field.

12. A process for producing edible beans for consumption, comprising processing the plurality of the edible bean seeds of claim 10 such that the plurality of the edible bean seeds are suitable for consumption.

13. A method for producing an edible bean seed designated as a Vibrant-derived edible bean seed, comprising:
    crossing a plant of edible bean seed designated as Vibrant, wherein a representative sample of the seed was deposited under the National Center for Genetic Resources Preservation accession number PI 673082, with a second edible bean plant to yield progeny edible bean seed; and
    growing the progeny edible bean seed to yield Vibrant-derived edible bean plants and allowing seed of Vibrant-derived edible beans plants to form.

14. The method of claim 13, wherein the second edible bean plant is transgenic.

15. An F1 edible bean designated as Vibrant-derived edible bean plant produced by the method of claim 13.

* * * * *